(12) United States Patent
Rhodes (10) Patent No.: US 11,191,859 B2
(45) Date of Patent: Dec. 7, 2021

(54) STERILIZATION TRAY

(71) Applicant: ASP Global Manufacturing GmbH, Schaffhausen (CH)

(72) Inventor: Samuel J. Rhodes, Los Angeles, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 620 days.

(21) Appl. No.: 15/858,576

(22) Filed: Dec. 29, 2017

(65) Prior Publication Data

US 2019/0201569 A1 Jul. 4, 2019

(51) Int. Cl.
| | |
|---|---|
| *A61L 2/20* | (2006.01) |
| *A61L 2/26* | (2006.01) |
| *A61B 50/33* | (2016.01) |
| *A61B 50/00* | (2016.01) |
| *A61B 90/70* | (2016.01) |

(52) U.S. Cl.
CPC .............. *A61L 2/208* (2013.01); *A61B 50/33* (2016.02); *A61L 2/26* (2013.01); *A61B 2050/0056* (2016.02); *A61B 2090/701* (2016.02); *A61L 2202/182* (2013.01); *A61L 2202/24* (2013.01)

(58) Field of Classification Search
CPC ............ A61L 2/26; A61L 2/208; A61B 50/33
See application file for complete search history.

(56) References Cited

U.S. PATENT DOCUMENTS

| | | | |
|---|---|---|---|
| 5,165,503 | A | 11/1992 | Hoffman |
| 5,348,711 | A | 9/1994 | Johnson et al. |
| 6,099,812 | A | 8/2000 | Allen et al. |
| 6,187,265 | B1 | 2/2001 | Wu et al. |
| 6,193,932 | B1 | 2/2001 | Wu et al. |
| 6,264,902 | B1 | 7/2001 | Howlett |

(Continued)

FOREIGN PATENT DOCUMENTS

| | | |
|---|---|---|
| CN | 1077651 A | 10/1993 |
| CN | 1168123 A | 12/1997 |

(Continued)

OTHER PUBLICATIONS

Chinese Search Report for Appication No. 201811624997.2 dated Apr. 24, 2021, 3 Pages.

(Continued)

*Primary Examiner* — Kevin Joyner
(74) *Attorney, Agent, or Firm* — Etan S. Chatlynne; Roberts Calderon Safran & Cole P.C.

(57) ABSTRACT

A sterilization tray is disclosed herein that may be used to facilitate preparation of an endoscope for sterilization and increase the likelihood that the endoscope will be properly sterilized. The sterilization tray may be fabricated from a flexible and vapor-permeable sheet. Cutouts may be disposed through the sheet to define standoffs that are foldable away from the sheet. A first standoff may include a first contoured portion disposed therein. The tray may also include a second standoff that has a second contoured portion and a third contoured portion disposed therein. The third standoff may include a locking tab disposed on a free end of the third standoff. A positioning tab may also be disposed on the third standoff. The sterilization tray may also include a dry booster to which an endoscope may be connected.

17 Claims, 6 Drawing Sheets

(56) References Cited

U.S. PATENT DOCUMENTS

| | | | |
|---|---|---|---|
| 6,379,631 B1 | 4/2002 | Wu | |
| 6,451,255 B1 | 9/2002 | Williams et al. | |
| 6,572,819 B1 | 6/2003 | Wu et al. | |
| 6,692,693 B2 | 2/2004 | Wu | |
| 7,229,591 B2 | 6/2007 | Wu et al. | |
| 7,300,638 B2 | 11/2007 | Williams et al. | |
| 8,915,363 B2* | 12/2014 | Hawkes | A61C 19/02 206/370 |
| 10,472,122 B2* | 11/2019 | Aguirre | B65D 5/445 |
| 2002/0191938 A1 | 12/2002 | Sheetz et al. | |
| 2004/0091389 A1 | 5/2004 | Malkin et al. | |
| 2005/0000553 A1 | 1/2005 | Noguchi et al. | |
| 2016/0009439 A1* | 1/2016 | Armstrong | B65D 5/003 206/509 |
| 2017/0224434 A1 | 8/2017 | Schwartzbauer et al. | |

FOREIGN PATENT DOCUMENTS

| | | |
|---|---|---|
| CN | 1878496 A | 12/2006 |
| CN | 203370791 U | 1/2014 |
| CN | 204173314 U | 2/2015 |
| CN | 205916483 U | 2/2017 |
| EP | 1 110 558 A2 | 6/2001 |
| EP | 2 138 127 A1 | 12/2009 |
| JP | S58180130 A | 10/1983 |
| TW | 537906 B | 6/2003 |
| WO | 01/17856 A1 | 3/2001 |
| WO | 2004/043499 A2 | 5/2004 |
| WO | 2013/119850 A1 | 8/2013 |
| WO | 2014089420 A1 | 6/2014 |
| WO | 2016/010970 A1 | 1/2016 |

OTHER PUBLICATIONS

English Translation of Chinese First Office Action for Appication No. 201811624997.2 dated May 6, 2021, 8 Pages.

Chinese First Office Action for Appication No. 201811624997.2 dated May 6, 2021, 4 Pages.

* cited by examiner

STERILIZATION TRAY

CROSS-REFERENCE TO CO-PENDING APPLICATIONS

This application is a counterpart of U.S. patent application Ser. No. 15/828,654, filed Dec. 1, 2017; Ser. No. 15/830,331, filed Dec. 4, 2017; Ser. No. 15/834,233, filed Dec. 7, 2017; Ser. No. 15/844,237, filed Dec. 15, 2017; and Ser. No. 15/858,381, filed Dec. 29, 2017, each of which are incorporated by reference in their entirety.

FIELD

The subject matter disclosed herein relates to containers used for sterilizing medical instruments.

BACKGROUND

Endoscopes are challenging to sterilize for various reasons. For example, because pressure within a lumen decreases from the lumen's inlet as a function of length and diameter, the pressure drop must be overcome to ensure that sterilant passes through the entire lumen and reaches all surfaces of the lumen. Further, lumens may collect debris or be blocked by fluids, such as rinse water.

A dry booster is a device that may be connected to a lumen of an elongate medical device, such as an endoscope. When subject to a sterilization process in which pressure changes are implemented, pressure differentials between the inside of a dry booster at one end of the lumen and a vacuum chamber at the other end of a lumen help pass a sterilant through the lumen, which assists in sterilizing the lumen.

SUMMARY

A sterilization tray is disclosed herein. The sterilization tray may be fabricated from a flexible and vapor-permeable sheet. Cutouts may be disposed through the sheet to define standoffs that are foldable away from the sheet. A first standoff may include a first contoured portion disposed therein. A score line may be disposed upon the sheet that extends between two edges of the first standoff. The tray may also include a second standoff that has a second contoured portion and a third contoured portion disposed therein. The third standoff may include a locking tab disposed on a free end of the third standoff. A positioning tab may also be disposed on the third standoff.

The sterilization tray may also be comprised of a top portion, a side portion, a bottom portion, a second score line, and a third score line. The second score line may distinguish the top portion from the side portion. The third score line may distinguish the bottom portion from the side portion. The top portion may include a slit. The third standoff may be disposed through the slit such that the locking tab engages the top portion The sterilization tray may also include a dry booster. A first tube may be connected to the dry booster and a second tube may also be connected to the dry booster. An adapter may be connected to the first tube and the second tube. The adapter may mate with a port on a control body of an endoscope.

The sterilization tray may be used to assist in sterilizing an endoscope according to the following methods and variations. The sterilization tray may be provided. Then, the first standoff may be folded away from the sheet and a first portion of the endoscope may be positioned upon the first standoff. Specifically, the first portion of the endoscope, which may be a control body of the endoscope, may be positioned upon the contoured portion of the first standoff. A second portion of the endoscope may also be positioned on the tray. Specifically, the second portion of the endoscope, which may be a portion of an insertion tube of the endoscope, may be disposed in contact with the second contoured portion and the third contoured portion of the second standoff. Next, the locking tab of the third standoff may be inserted through the slit to restrict movement of the top portion relative to the bottom portion. In some variations, a dry booster may be attached to the sterilization tray and the endoscope may be attached to the dry booster.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Successful sterilization of an endoscope may require accounting for various challenges. Sterilization trays for endoscopes may be designed to increase the likelihood that an endoscope may be successfully sterilized during a sterilization procedure by addressing each of the following three sterilization challenges. First, endoscopes are cumbersome to handle. Second, endoscope tubes are typically made from polyurethane, which absorbs sterilants such as hydrogen peroxide. When one portion of an endoscope tube touches another portion of the endoscope tube, or any other material or object that absorbs sterilant, a so-called "mated surface" is formed, which effectively provides additional mass through which a sterilant must penetrate to achieve sterilization. Third, endoscopes include multiple long and narrow lumens that may restrict the flow of a sterilant therethrough.

Figure 1:
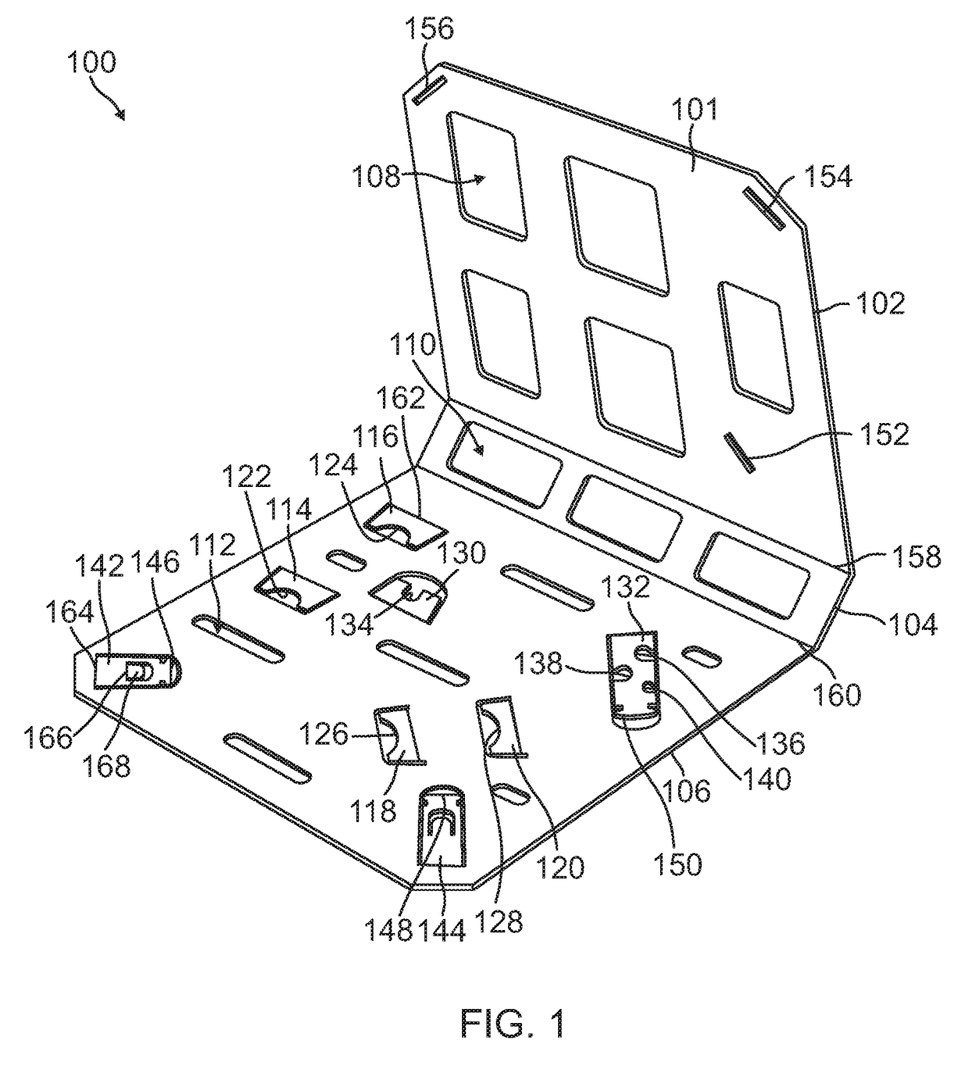
FIG. 1 depicts a perspective view of a sterilization tray.
Figure 2:
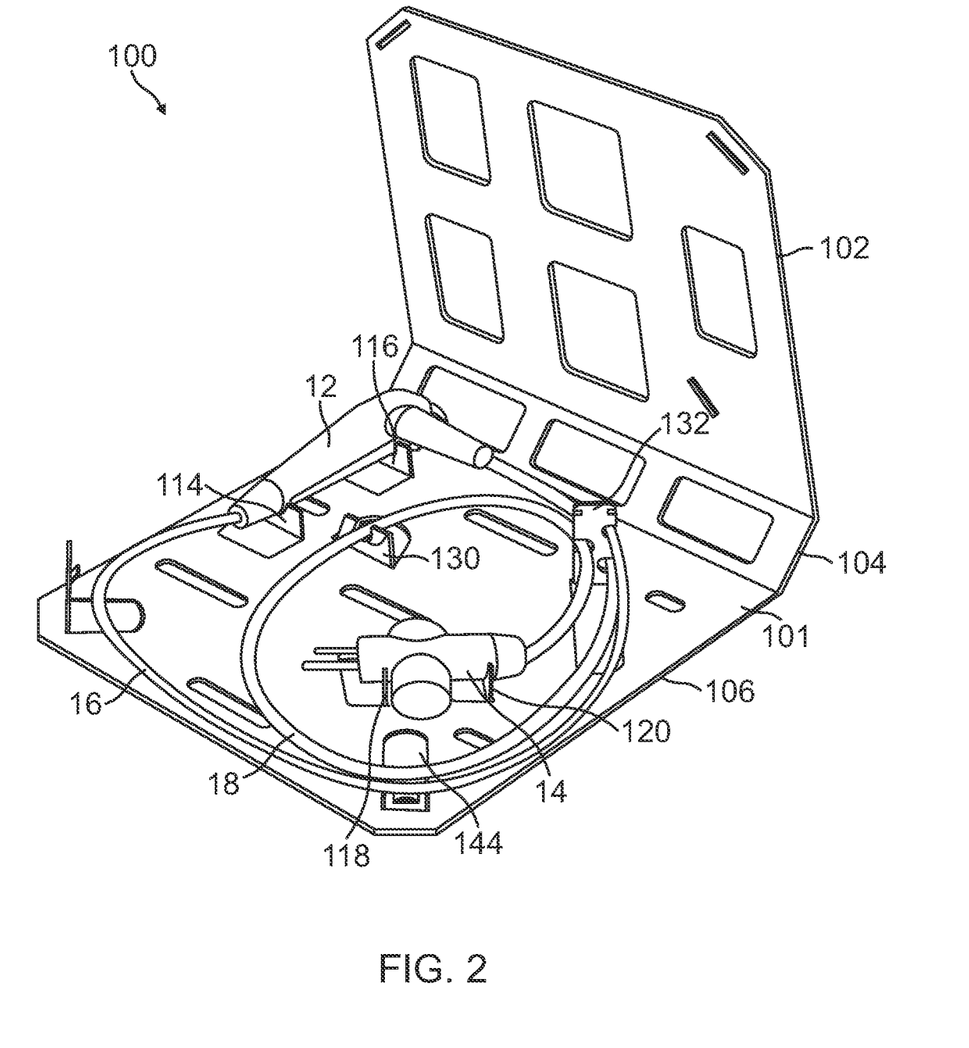
FIG. 2 depicts a perspective view of the sterilization tray of FIG. 1 containing an endoscope.
Figure 3:
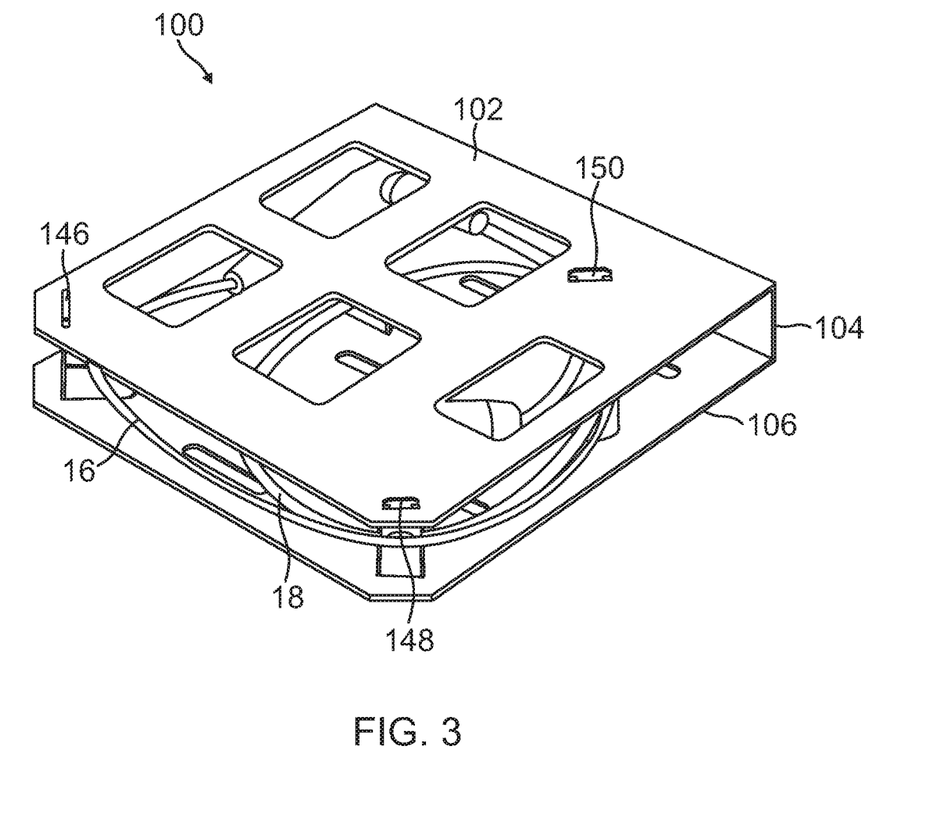
FIG. 3 depicts a perspective view of the sterilization tray of FIG. 1 in a closed configuration and containing the endoscope.

Disclosed herein is a tray or container that may address the foregoing challenges to endoscope sterilization. Referring to FIGS. 1-3, tray 100 may be provided as a single component fabricated from a sheet 101 of a material that is preferably light weight and vapor permeable, particularly to gaseous sterilants, such as hydrogen peroxide. High density polyethylene is a suitable material. Sheet 101 may include a top portion 102, a side portion 104, and a bottom portion 106. Various vent holes, e.g., holes 108, 110, and 112, may be disposed though portions 102, 104, and 106, respectively, to minimize weight and material use, and also to minimize restrictions to sterilant flow through and about tray 100.

Various cutouts may be disposed through lid portion 106 to define edges of features or standoffs for maintaining a position of an endoscope that may include, e.g., a control body 12, a light-guide connector body 14, an insertion tube 16, and an umbilical tube 18. For example, bottom portion 106 may include a first standoff 114 and a second standoff 116 that may support control body 12, and a third standoff 118 and a fourth standoff 120 that may support light-connector body 14. Each standoff 114, 116, 118, and 120 may have a contoured portion—respectively 122, 124, 126, and 128—that facilitates proper placement and orientation of bodies 12 and 14 upon the standoffs. Bottom portion 106 may also include a fifth standoff 130 and sixth standoff 132 that may support insertion tube 16 and umbilical tube 18. Fifth standoff 130 and sixth standoff 132 may include one or more contoured portions to facilitate placement and orientation of insertion tubes 16 and umbilical tube 18. For example, as shown, fifth standoff 130 includes a single contoured portion 134 whereas sixth standoff 132 includes three contoured portions 136, 138, and 140. Referring to FIG. 2, umbilical tube 18 is supported by contoured portions 134, 136, and 138, and insertion tube 16 is supported by contoured portion 140.

Additional standoffs, e.g., seventh standoff 142 and eighth standoff 144, may be provided with additional or alternative functionality. In the embodiments reflected in the figures, seventh standoff 142 includes a pair of locking tabs 146 disposed on its free end (i.e., the end not connected to sheet 101), and eighth standoff 144 includes a pair of locking tabs 148 disposed on its free end. As shown, a pair of locking tabs 150 is also included upon sixth standoff 132. Locking tabs 146, 148, and 150 may mate with slits 152, 154, and 156, which are disposed on top portion 102. That is, standoffs 132, 142 and 144 may be disposed through slits 152, 154, and 156 such that locking tabs 146, 148, and 150 may engage top portion 102. The portion of each standoff containing the locking tabs may be wider than the slits such that resistance to motion of top portion 102 may be provided by the locking tabs. Thus, locking tabs 146, 148, and 150 may be used to restrict movement of top portion 102 relative to bottom portion 106, such that tray 100 may be placed into a closed or assembled configuration, which is reflected in FIG. 3. Standoffs 142 and 144 may further include positioning tabs 168 and 170, respectively. Positioning tabs 168 and 170 may help avoid inserting standoffs 142 and 144 too far through slits 156 and 154. Alternatively or additionally, positioning tabs 160 and 170 may be used to support a portion of an endoscope. For example, although not shown in the figures, positioning tab 168 may be used to support a portion of insertion tube 16 and positioning tab 170 may be used to support a portion of insertion tube 16 or umbilical tube 18.

Referring to FIGS. 2 and 3, standoffs 114, 116, 118, 120, 130, 132, and 144, as well as their contoured portions, may be used to position an endoscope's control body 12 and light connector body 14, as well as route insertion tube 16 and umbilical tube 18 into a configuration in which one portion of the endoscope does not contact any other portion of the endoscope. As seen, insertion tube 16 and umbilical tube 18 are maintained in a coiled configuration in which they do not contact each other. For example, standoff 132 maintains the position of umbilical tube 18 at two locations and the position of insertion tube 16 at one location. Further, standoff 144 may be used to space umbilical tube 18 from insertion tube 16 as best seen in FIG. 3. Accordingly, tray 100 helps avoid the mated-surfaces problem described above caused by one portion of the endoscope contacting another portion of the endoscope.

The various features, e.g., vent holes and standoffs, may be formed by removing material (e.g., by laser cutting or stamping) from sheet 101. Further, sheet 101 may be scored at locations to form score lines, e.g., score lines 158, 160, 162, 164, and 166, to facilitate folding tray 100 out of its open or unassembled configuration of FIG. 1 and into its closed or assembled configuration of FIG. 3. For example, score lines 158 and 160 may extend the width of sheet 101 and distinguish side portion 104 from top portion 102 and bottom portion 106. Further for example, score lines 162, 164, and 166 may be disposed upon sheet 101 and extend between cutouts defining standoff 116, standoff 142, and positioning tab 168.

In alternate embodiments, the sterilization tray may include a dry booster. Dry boosters are described in U.S. Pat. Nos. 6,451,255 and 7,229,591, which are hereby incorporated by reference in their entirety. In short, dry boosters may be used to create a pressure differential between a so-called "booster" volume and the vacuum chamber of a sterilizer to assist in introducing and removing sterilant through a lumen, such as a lumen in insertion tube 16 or umbilical tube 18 that connects the booster volume and the vacuum chamber.

Figure 4:
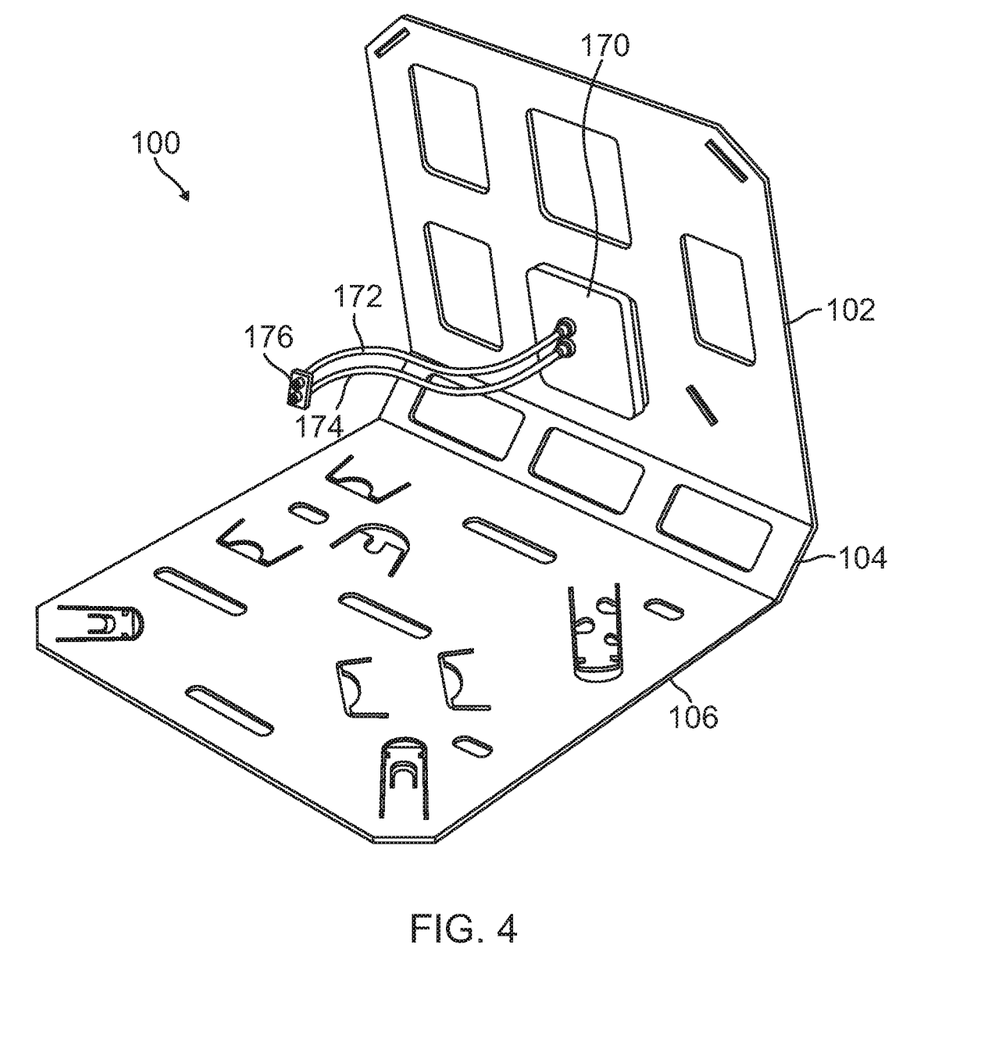
FIG. 4 depicts a perspective view of the sterilization tray of FIG. 1 with a dry booster disposed therein.
Figure 5:
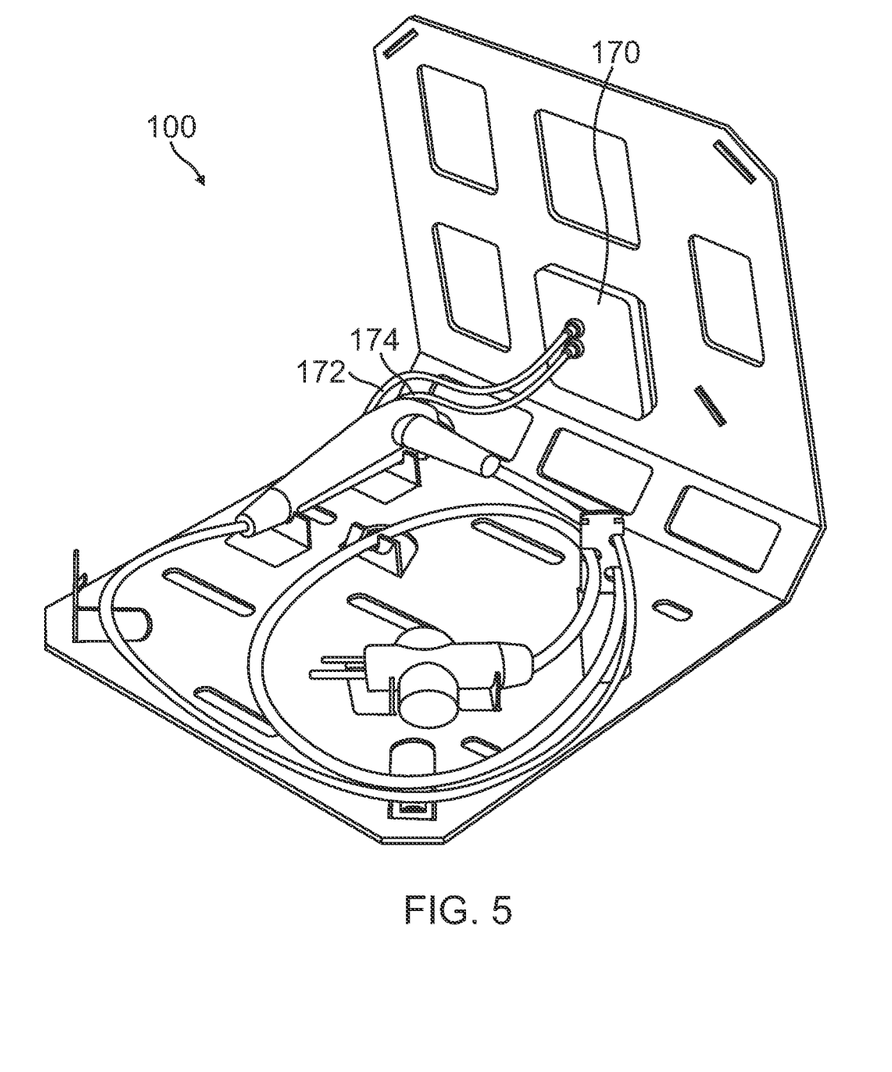
FIG. 5 depicts a perspective view of the sterilization tray of FIG. 4 containing an endoscope.
Figure 6:
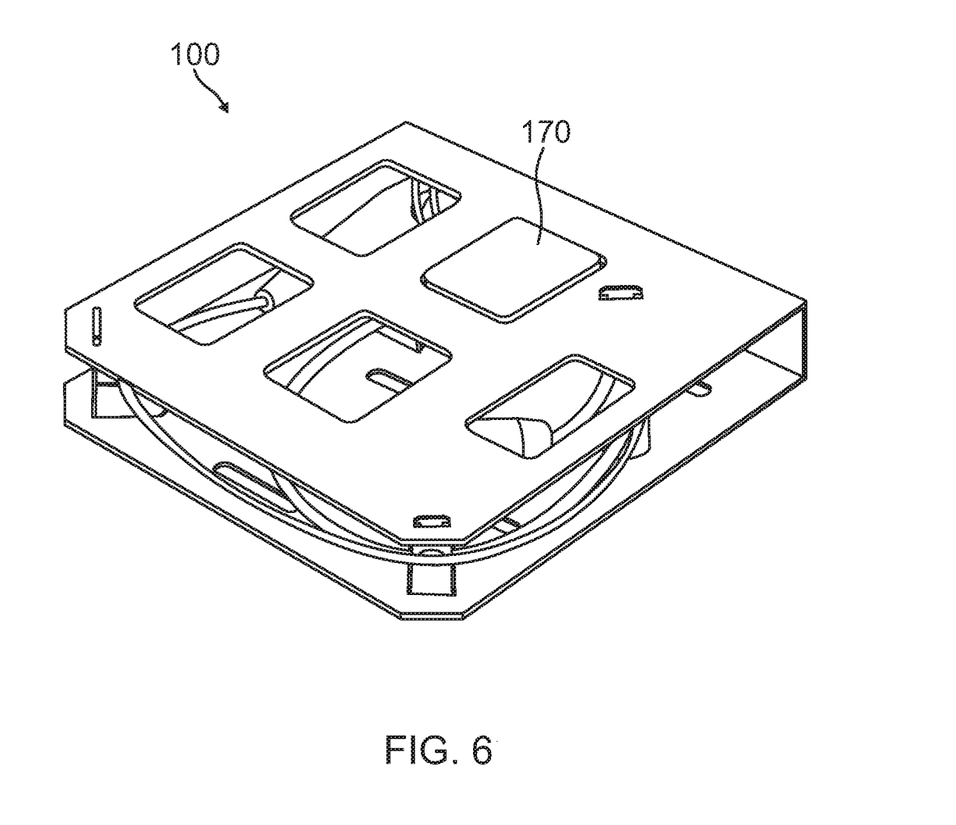
FIG. 6 depicts a perspective view of the sterilization tray of FIG. 4 in a closed configuration and containing the endoscope.

As shown in FIGS. 4-6, tray 100 may be outfitted with a dry booster 170. Dry booster 170 may have a channel formed thereon that may mate with the edges of a vent hole in top portion 102 such that dry booster 170 may be disposed therein. A first tube 172 and a second tube 174 may be connected on one end to dry booster 170. In other embodiments, dry booster 170 may include additional tubes, e.g., a third tube and a fourth tube. The other ends of tubes 172 and 174 (and any additional tubes) may be connected to an adapter 176. Adapter 176 may be configured to mate with ports (not shown) on control body 12 of an endoscope. These ports may provide access to one or more lumens within insertion tube 16 and/or umbilical tube 18. Accordingly, when adapter 176 is connected to ports on control body 12, one or more lumens in tubes 16 and/or 18 are placed in fluid communication with an internal volume defined by dry booster 170. As described in U.S. patent application Ser. No. 15/844,237 filed Dec. 15, 2017, the contents of which are incorporated by reference herein in their entirety, the lengths and diameters of tubes 172 and/or 174 (and/or any additional tubes) may be chosen to provide flow-restriction to sterilant passing therethrough to help ensure that proper amounts of sterilant pass through each lumen in the endoscope.

A manufacturer of tray 100 may assemble dry booster 170 therein before providing it to a user (e.g., healthcare provider). Alternatively, a manufacturer or tray 100 may provide tray 100 and dry booster 170 to a user who installs dry booster 170 into tray 100.

A sterilization tray, e.g., tray 100, with an endoscope disposed therein may be subject to a sterilization cycle within a vacuum chamber of a sterilizer, such as the STERRAD® System, STERRAD® NX System or STERRAD® 100NX System of Advanced Sterilization Products, Division of Ethicon US, LLC, a Johnson & Johnson company. In those embodiments including a dry booster, the dry booster may assist the sterilizer in sterilizing the endoscope. As pressure is lowered within the vacuum chamber, the pressure within the dry booster concomitantly drops, but lags behind the pressure in the vacuum chamber because of the time required to withdraw gas from the dry booster and through insertion tube 16. Similarly, when pressure within the vacuum chamber is raised, the pressure within the dry booster concomitantly rises, but it lags behind the pressure in the vacuum chamber because of the time required to pass gas into the dry booster, through insertion tube 16. Accordingly, when pressure within the vacuum chamber is raised by introducing a gaseous sterilant into the vacuum chamber, the lower pressure within the dry booster provides suction through the lumens of insertion tube 16, which may assist sterilant penetrating throughout the lumens. Similarly, when pressure is lowered in the vacuum chamber, suction through the lumens may assist in flushing or removing any residual sterilant or moisture from the lumens.

A sterilization tray as disclosed herein may be used according to the following method and variations. First, a tray (e.g., tray 100) may be provided. In some variations, the tray may be provided having the form of a sheet. Second, a dry booster may be assembled onto the tray, either by a manufacturer or user (e.g., healthcare provider), to form a tray having a dry booster. For example, dry booster 170 may be installed into a vent hole of top portion 102. Third, the standoffs of bottom portion 106, e.g., standoffs 114, 116, 118, 120, 132, 142, and 144, may be folded such that they extend away (e.g., transversely) from bottom portion 106. In those embodiments that include score lines (e.g., score lines 162 and 164), the standoffs may be folded about the score lines. Further, in those embodiments that include positioning tabs, e.g., positioning tabs 168 and 170, the positioning tabs may be folded out of their respective standoffs. Fourth, for those trays including dry booster 170, first tube 172 and second tube 174 may be connected to ports of an endoscope's control body 12 to place the endoscope's lumens in fluid communication with the inside of dry booster 170. In some variations, this connection may be accomplished by using adapter 176, which is connected to tubes 172 and 174 and is configured to mate to the ports. Fifth, an endoscope's control body 12 may be disposed upon at least two of the standoffs, e.g., standoffs 114 and 116. Sixth, the endoscope's insertion tube 16 and umbilical tube 18 may be disposed in a coiled configuration using the standoffs, e.g., standoffs 132 and 144. Seventh, insertion tube 16 and umbilical tube 18 may be checked for mated surfaces, e.g., to confirm that no portion of insertion tube 16 contacts any portion of umbilical tube 18. Eighth, the tray may be folded out of its open or unassembled configuration (FIG. 1) to its closed or assembled configuration (FIG. 3) such that side portion 104 extends away (e.g., transversely) from bottom portion 106 and such that top portion 102 is spaced from but parallel to bottom portion 106. In those embodiments including score lines, e.g., score lines 158 and 160, the tray may be folded at these score lines. Ninth, locking tabs (e.g., tabs 146, 148, and 150) may be passed through slits disposed through top portion 102 (e.g., slits 152, 154, and 156). The standoffs containing these locking tabs may be bent to assist in passing the locking tabs through the slits. After the locking tabs have been passed through the slits, the standoffs may become unbent due to resilience of the tray material. Tenth, sterilization tray 100, with the endoscope disposed therein, may be placed into a sealable and vapor permeable pouch made from, e.g., DuPont™ Tyvek®. Alternatively or additionally, sterilization tray 100 may be wrapped using a sterilization wrap, such as KIMBERLY-CLARK* KIMGUARD* Sterilization Wrap. Ninth, tray 100 with the endoscope disposed therein, may be placed into a vacuum chamber of a sterilizer. Eleventh, the tray with the endoscope disposed therein may be subject to a sterilization cycle. Twelfth, pressure in the vacuum chamber may be lowered. Thirteenth, a sterilant, e.g., hydrogen peroxide, may be introduced into the chamber. Fourteenth, the sterilant may be drawn through insertion tube 16 and into volume or chamber 108 assisted by a pressure differential between dry booster 170 and the vacuum chamber. Fifteenth, the vacuum chamber may be vented to raise the pressure and introduce another gas, e.g., air, therein. This gas may be drawn through insertion tube 16 and into dry booster 170 assisted by a pressure differential between dry booster 170 and the vacuum chamber, which may assist in flushing the sterilant from the lumen. Sixteenth, pressure in the vacuum chamber may be lowered. Gas within dry booster 170 may be drawn through insertion tube 16 and into the vacuum chamber, which may further assist in flushing the sterilant from the lumen. Seventeenth, tray 100 may be removed from the vacuum chamber of the sterilization system.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

I claim:

1. A sterilization tray, comprising:
    a flexible and vapor-permeable sheet comprising a top portion, a side portion, and a bottom portion;
    a cutout disposed through the bottom portion, the cutout defining an outer periphery of a first standoff that is foldable away from the bottom portion;
    a first contoured portion disposed through the first standoff; and
    an endoscope, at least a portion of which is positioned on the first standoff.

2. The sterilization tray of claim 1, further comprising a first score line disposed upon the bottom portion and extending between two edges of the first standoff.

3. The sterilization tray of claim 2, further comprising a second standoff including at least a second contoured portion and a third contoured portion.

4. The sterilization tray of claim 3, further comprising a third standoff including a locking tab disposed on a free end of the third standoff.

5. The sterilization tray of claim 4, further comprising a positioning tab disposed on the third standoff.

6. The sterilization tray of claim 4, further comprising a second score line and a third score line, the second score line distinguishing the top portion from the side portion, and the third score line distinguishing the bottom portion from the side portion.

7. The sterilization tray of claim 6, wherein the top portion further includes a slit, and the third standoff is disposed through the slit such that the locking tab engages the top portion.

8. The sterilization tray of claim 1, further comprising a dry booster.

9. The sterilization tray of claim 8, further including a first tube connected to the dry booster and a second tube connected to the dry booster.

10. The sterilization tray of claim 9, further including an adapter connected to the first tube and the second tube.

11. A method of sterilizing an endoscope comprising:
   providing a sterilization tray, the sterilization tray including
      a flexible and vapor-permeable sheet comprising a top portion, a side portion, and a bottom portion, and
      a cutout disposed through the bottom portion, the cutout defining a first standoff that is foldable away from the bottom portion;
   folding the first standoff away from the bottom portion; and
   positioning a first portion of the endoscope upon the first standoff.

12. The method of claim 11, wherein the first standoff further comprises a first contoured portion, and
   the step of positioning the first portion of the endoscope upon the first standoff includes positioning the first portion of the endoscope in contact with the first contoured portion.

13. The method of claim 12, wherein the bottom portion further includes a second standoff having at least a second contoured portion and a third contoured portion, and the method further includes:
   positioning a second portion of an endoscope in contact with the second contoured portion and a third portion of an endo scope in contact with the third contoured portion.

14. The method of claim 13, wherein the first portion of the endoscope is a portion of a control body and the second portion of the endoscope is a portion of an insertion tube.

15. The method of claim 14, wherein the sheet further includes
   a slit through the top portion, and
   a third standoff disposed through the bottom portion, the third standoff including a locking tab; and
   the method further includes
      inserting the third standoff through the slit, and
      restricting movement of the top portion relative to the bottom portion with the locking tab.

16. The method of claim 11, further comprising attaching a dry booster to the sterilization tray.

17. The method of claim 16, further comprising attaching a dry booster to the endoscope.

* * * * *